(12) United States Patent
Ho et al.

(10) Patent No.: US 7,087,790 B2
(45) Date of Patent: Aug. 8, 2006

(54) BENZOTROPOLONE DERIVATIVES AND MODULATION OF INFLAMMATORY RESPONSE

(75) Inventors: Chi-Tang Ho, East Brunswick, NJ (US); Geetha Ghai, Murray Hill, NJ (US); Shengmin Sang, East Brunswick, NJ (US); Jin-Woo Jhoo, Little Rock, AR (US); Mou-Tuan Huang, Englewood Cliffs, NJ (US); Robert T. Rosen, Monroe Township, NJ (US); Slavik Dushenkov, Fort Lee, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 10/652,813

(22) Filed: Aug. 29, 2003

(65) Prior Publication Data

US 2005/0049284 A1  Mar. 3, 2005

(51) Int. Cl.
  *C07C 45/00*   (2006.01)
  *C07C 49/115*  (2006.01)
  *C07D 311/78*  (2006.01)
  *C07D 315/00*  (2006.01)
  *A61K 31/00*   (2006.01)

(52) U.S. Cl. .................. 568/311; 568/327; 549/381; 549/416; 514/681; 514/732

(58) Field of Classification Search ............... 568/311, 568/327; 514/681, 732, 738; 549/381, 416
See application file for complete search history.

(56) References Cited

U.S. PATENT DOCUMENTS

| | | | | |
|---|---|---|---|---|
| 3,812,266 | A * | 5/1974 | Sanderson et al. ............ | 426/52 |
| 5,861,415 | A | 1/1999 | Majeed et al. ............... | 514/321 |
| 5,998,437 | A | 12/1999 | Nishi et al. .................. | 514/314 |
| 6,113,965 | A | 9/2000 | Goodsall et al. ............ | 426/425 |
| 6,348,224 | B1 | 2/2002 | Patil et al. .................... | 426/49 |
| 6,469,053 | B1 | 10/2002 | Romanczyk, Jr. et al. .. | 514/456 |
| 6,482,450 | B1 * | 11/2002 | Goodsall et al. ............. | 426/52 |
| 6,491,943 | B1 | 12/2002 | Tsuji et al. ................. | 424/439 |
| 6,524,630 | B1 | 2/2003 | Schmitz ....................... | 424/776 |

FOREIGN PATENT DOCUMENTS

WO    WO 01/21137 A1    3/2001

OTHER PUBLICATIONS

Sang et al. Theadibenzotropolone A, a new type of pigment from enzymatic oxidation of (-) epicatechin and (-) epigallocatechin gallate and characterized from black tea using LC/MS/MS.□□Tetrahedron Letters, vol. 43, 2002, p. 7129-7133.*

Araujo et al., Biological Activities of *Curcuma Ionga* L., Mem Inst Oswaldo Cruz, Rio de Janeiro, vol. 96, No. 5, Jul. 2001, pp. 723-728.

Hiipakka et al., Structure-activity relationships for inhibitions of human 5α-reductases by polyphenols, Biochemical Pharmacology, vol. 63, 2002, pp. 1165-1176.

Marnett et al., COX-2: A Target for Colon Cancer Prevention, Annu. Rev. Pharacol. Toxicol., vol. 42, 2002, pp. 55-80.

Acker, S.A.B.E.V.; Berg, D.J.V.D.; Tromp, M.N.J.L.; Griffioen, D. H.; Bennekom, W.P.V.; Der Vijgh, W.J.F.V.; Bast, A. Structural aspects of antioxidant activity of flavonoids. Free Radical Biol. Med. 1996, 20, 331-342.

Balentine, D. A.; Wiseman, S.A.; Bouwens, L.C.M. The chemistry of tea flavonoids, Critical Reviews in Food Science and Nutrition. 1997, 37, 693-704.

Berkowitz, J.E.; Coggon, P; Sanderson, G.W. Formation of epitheaflavic acid and its transformation to thearubigins during tea fermentation. Phytochemistry. 1971, 10, 2271-2278.

Bryce, T.; Collier, P.D.; Fowlis, I.; Thomas, P.E.; Frost, D.; Wilkins, C.K. The structures of the theaflavins of black tea. Tetrahedron letters. 1970, 32, 2789-2792.

Cao, G.; Alessio, H.M.; Cutler, R.G. Oxygen-radical absorbance capacity assay for antioxidants, Free Radical Biol. Med. 1993, 14, 303-311.

Coxon, D.T.; Holmes, A.; Ollis, W.D. Isotheaflavin. A new black tea pigment. Tetrahedron letters. 1970, 60, 5241-5246.

Coxon, D. T.; Holmes, A.; Ollis, W.D.; Vora, V.C. The constitution and configuration of the theaflavin pigments of black tea, Tetrahedron letters. 1970, 60, 5237-5240.

(Continued)

*Primary Examiner*—Sikarl A. Witherspoon
(74) *Attorney, Agent, or Firm*—Jones Day

(57) ABSTRACT

The present invention provides novel benzotropolone derivatives represented by the general formula:

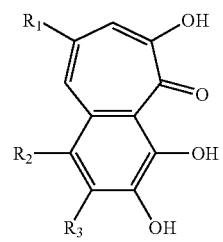

including neotheaflavate B and EGCGCa. The benzotropolone derivatives of the present invention are effective antioxidant and anti-inflammatory agents. The present invention also provides novel method of synthesizing benzotropolone compounds in high yields and method of treating inflammatory conditions using benzotropolone containing compounds.

26 Claims, No Drawings

OTHER PUBLICATIONS

Collier, P.D.; Mallows, B.R.; Thomas, P.E.; Frost, D.J.; Korver, O.; Wilkins, C.K. The theaflavins of black tea. Tetrahedron. 1973, 29, 125-142.

Galati, G.; Teng, S.; Moridani, M.Y.; Chan, T.S.; O'Brien, P.J. Cancer chemoprevention and apoptosis mechanisms induced by dietary polyphenolics. Drug metabolism and Drug interaction. 2000, 17, 311-349.

Guo, Q.; Zhao, B.; Shen, S.; Hou, J.; Hu, J.; Xin, W. ESR study on the structure-antioxidant activity relationship of tea catechins and their epimers. Biochimica et Biophysica Acat. 1999, 1427, 13-23.

Halder, J.; Tamuli, P; Bhaduri, A.N. Isolation and characterization of polyphenol oxidase from indian tea leaf (Camellia Sinensis). Nutritional Biochemistry. 1998, 9, 75-80.

Halder, J.; Bhaduri, A. N. Protective role of black tea against oxidative damage of human red blood cells, Biochemical and Biophysical Research Communications. 1998, 244, 903-907.

Jovanovic, S.V.; Hara, Y.; Steenken, S.; Simic, M. Antioxidant potential of theaflavins. A pulse radiolysis study. J. Am. Chem. Soc. 1997, 119, 5337-5343.

Katiyar, S.K.; Mukhtar, H. Tea antioxidants in cancer chemoprevention. Journal of cellular biochemistry supplement. 1997, 27, 59-67.

Kondo, K.; Kurihara, M.; Fukuhara, K. Mechanism of antioxidant effects of catechins. Methods of Enzmology. 2001,335, 203-217.

Kuroda, Y.; Hara, Y. Antimutagenic and anticarcinogenic activity of tea polyphenols. Mutation Research, 1999, 436, 69-97.

Leung, L.K.; Su, Y.; Chen, R; Zhang, Z.; Huang, Y.; Chen, Z.Y. Theaflavins in black tea and catechins in green tea are equally effective antioxidants. American Society for Nutritional Sciences. 2001, 2248-2251.

Lewis, J.R.; Davis, A.L.; Cai, Y.; Davies, A.P.; Wilkins, J.P.G.; Pennington M. Theaflavate B, Isotheaflavin-3'-O-gallate, neotheaflavin-3-O-gallate: three polyphenolic pigments from black tea. Phytochemistry. 1998, 49, 2511-2519.

Lin, Y.L.; Tasi, S.H.; Lin-Shiau, S.Y.; Ho, C.T.; Lin, J.K. Theaflavin-3,3'-digallate from black tea blocks the nitric oxide synthase by down-regulating the activation of NF-kB in macrophages. European Journal of Pharmacology. 1999, 367, 379-388.

Miller, N.J.; Castelluccio, C.; Tijburg, L.; Rice-Evans, C. The antioxidant properties of theaflavins and their gallate esters-radical scavengers or metal chelators? FEBS letters. 1996, 392, 40-44.

Nonaka, G.I.; Hashimoto, F; Nishioka, I. Tannins and related compounds. XXXVI. Isolation and structures of theaflagallins, new red pigments from black tea. Chem. Pharm. Bull. 1986, 34, 61-65.

Obanda, M.; Owuro, P O.; Mang'oka, R. Changes in the chemical and sensory quality parameters of black tea due to variation of fermentation time and temperature. Food Chemistry. 2001, 75, 395-404.

Ou, B.; Hampsch-Woodill, M.; Prior, R.L. Development and validation of an improved oxygen radical absorbance capacity assay using fluorescein as the fluorescent prob. J. Agric. Food Chem. 2001, 49, 4619-4626.

Robertson A. Effects of physical and chemical conditions on the in vitro oxidation of tea leaf catechins. Phytochemistry. 1983, 22, 889-896.

Robertson A. The chemistry and biochemistry of black tea production—the non-volatiles. Instant Tea, Cultivation to Consumption, Champman & Hall: London, UK. 1992, 555-601.

Roberts, E.A.H.; Cartwright, R.A.; Oldschool, M. The phenolic substances of manufactured tea. I.-fractionation and paper chromatography of water-soluble substances. J. Sci. Food Agric. 1957, 8, 72-80.

Sarkar, A.; Bhaduri, A. Black tea is a powerful chemopreventor of reactive oxygen and nitrogen species : comparison with its individual catechin constituents and green tea. Biochemical and Biophysical Research Communication. 2001, 284,173-178.

Shiraki, M.; Hara, Y.; Osawa, T.; Kumon, H.; Nakayama, T.; Kawakishi, S. Antioxidative and antimutagenic effects of theaflavins from black tea. Mutat. Res. 1994, 323, 29-34.

Takino, Y.; Imagawa, H.; Horikawa, H.; Tanaka, A. Studies on the mechanism of the oxidation of tea leaf catechins—formation of the reddish orange pigment and its spectral relationship to some benzotropolone derivatives. Agricultural and Biological Chemistry. 1964, 28, 64-71.

Tanaka, T.; Inoue, K.; Betsumiya, Y; Mine, C.; Kouno, I. Two types of oxidative dimerization of the black tea polyphenol theaflavin. J. Agric. Food Chem. 2001, 49, 5785-5789.

Tanaka, T.; Mine, C.; Inoue, K.; Matsuda, M.; Kouno, I. Synethesis of theaflavin from epicatechin and epigallocatechin by plant homogenates and role of epiatechin quinone in the synthesis and degradation of theaflavin. J. Agric. Food Chem. 2002, 50, 2142-2148.

Valcic, S.; Muders, A.; Jacobsen, N. E.; Liebler, D.C.; Timmermann, B.N. Antioxidant chemistry of green tea catechins. Identification of products of the reaction of (-)-epigallocatechin gallate with peroxyl radicals. Chem. Res. Toxicol. 1999, 12, 382-386.

Wan, S.; Nurstren, H. E.; Cai, Y; Davis, A.L.; Wilkins, J.P. G.; Davis, A.P. A new type of tea pigment-from the chemical oxidation of epicatechin gallate and isolated from tea. J. Sci. Food Agric. 1997, 74, 401-408.

Wiseman, S.A.; Balentine, D.A.; Frei, B., Antioxidants in tea, Critical Reviews in Food Science and Nutrition, 1997, 37, 705-718.

Yang, C.S.; Chung, J. Y; Yang., G.Y.; Chhabra, S.K.; Lee, M.J. Tea and tea polyphenols in cancer prevention. J. Nutr. 2000, 130, 472-478.

Yoshida, H.; Ishikawa, T.; Hosoai, H.; Suzukawa, M.; Ayaori, M.; Hisada, T.; Sawada, S.; Yonemura, A.; Higashi, K.; Ito, T.; Nakajima, K.; Yamashita, T.; Tomiyasu, K.; Nishiwaki, M.; Ohsuzu, F.; Nakamura, H. Inhibitory effects of tea flavonoids on the ability of cells to oxidize low density lipoprotein. Biochemical Pharmacology. 1999, 58, 1695-1703.

Delgado, J. N. And W. A. Remers 1998. Wilson and Gisvold's Textbook of Organic Medicinal and Pharmaceutical Chemistry, Lippincott Williams & Wilkins Publishers.

Huang, M-T et al., Inhibitory effect of black tea constituents on 12-O-tetradecanoylphorbol-13-acetate induced inflammation, pro-inflammatory cytokine expression and arachidonic acid metabolism, for Cancer Research and Center for Advanced Food Technology, Rutgers University, Proceedings of the American Association for Cancer Research, vol. 44, 2003.

Vinson, Black and greet tea and heart disease: A review, 2000, Biofactors 13, 127-132.

Weisburger et al., Mechanisms of chronic disease causation by nutritional factors and tobacco products and their prevention by tea polyphenols, 2002, Food & Chemical Toxicology, 40, 1145-1154.

Yang et al., Black tea constituents, theaflavins, inhibit 4-(methylnitrosamino)- 1-(3-pyridyl)-1-butanone (NNK)-induced lung tumorigenesis in A/J mice, 1997, Carcinogenesis, 18, 2361-2365.

Liang et al., Inhibition of 12-O-Tetradecanoylphorbol-13-Acetate-Induced Inflammatory Skin Edema and Ornithine Decarboxylase Activity by Theaflavin-3,3'-Digallate in Mouse, 2002, Nutrition and Cancer, 42 (2), 217-223.

Sala et al., Assessment of the anti-inflammatory activity and free radical scavenger activity of tiliroside, 2003, European Journal of Pharmacology 461(1), 53-61.

Ukiya et al., Constituents of Compositae Plants. 2. Triterpene Diols, Triols, and Their 3-O-Fatty Acid Esters from Edible Chrysanthemum Flower Extract and Their Anti-inflammatory Effects, 2001, Journal of Agricultural and Food Chemistry 48(7), 3187-3197.

Huang et al., 2003, Protective effect of dibenzolmethane on chemically-and UV light-induced skin, inflammation, sunburn lesions, and skin carcinogenesis in mice, In: Food Factors in Health Promotion and Disease Prevention, Washington DC, American Chemical Society: 196-207.

Huang et al., Inhibitory Effect of Curcumin, Chlorgenic Acid, Caffeic Acid, and Ferulic Acid on Tumor Promotion in Mouse Skin by 12-O-Tetradecanoylphorbol-13-acetate, 1988, Cancer Research, 48, 5941-5946.

* cited by examiner

US 7,087,790 B2

BENZOTROPOLONE DERIVATIVES AND MODULATION OF INFLAMMATORY RESPONSE

FIELD OF THE INVENTION

The present invention relates to compounds that contain benzotropolone moieties and their use as antioxidants and anti-inflammatory pharmaceutical agents, as well as a novel method of making such compounds.

BACKGROUND OF THE INVENTION

A number of pharmaceutical agents have been developed for use as antioxidants and anti-inflammatory agents. These pharmaceutical agents, particularly anti-inflammatory agents, have adverse actions such as drowsiness, gastrointestinal troubles, and their continuous administration for a long period cause a problem. Because of these adverse reactions, there is a strong demand for antioxidant and anti-inflammatory pharmaceutical agents derived from natural products which can be administered long term, are safe, and cause no adverse reactions.

Tea (Camellia sinensis (L.) Kuntze) is one of the most popular beverages in the world. Tea leaf is known to be rich in flavonoids, including catechins, and their derivatives. which are polyphenols (a compound consisting of one aromatic ring which contains at least one hydroxyl group is classified as a simple phenol. A polyphenol therefore consists of more than one aromatic ring, and more than two hydroxyl groups).

Many studies have demonstrated that green tea and black tea polyphenols have anti-inflammatory, anti-cancer, and anti-cardiovascular disease activity (Vinson, 2000, Biofactors 13: 127–132; Weisburger et al., 2002, Food & Chemical Toxicology, 40:1145–1154.). These biological activities are believed to be due to their antioxidant activity through scavenging reactive oxygen species (ROS) and free radicals. Theaflavins have been regarded as one of the important biologically active components in black tea and the green tea catechins are of similar importance. Indeed, there are a number of reports disclosing the biological activities of theaflavins as a mixture. However, even though tea is consumed daily and in large quantities throughout the world, limited information is available concerning biological activity of individual tea components or their use as pharmaceutical agents.

There are a number of prior art references, which disclose compounds having chemical structural formulas to some of those disclosed in the present invention (Coxon et al., 1970, Tetrahedron Letters, 60: 5241–5246; Leung et al., 2001, The Journal of Nutrition, 2248–2251; Lewis et al., 1998, Phytochemistry, 49: 2511–2519; Lin et al., 1999, European Journal of Pharmacology, 376: 379–388; Miller et al., 1996, FEBS Letters, 392: 40–44; Obanda et al., 2001, Food Chemistry, 75: 395–404; Shiraki et al., 1994, Mutat. Res., 323: 29–34; Tanaka et al., 2001, J. Agric. Food Chem, 49: 5785–5789; Tanaka et al., 2002, J. Agric. Food Chem, 50: 2142–2148; Wan et. al., 1997, J. Sci. Food Agric., 74: 401–408; Wiseman et al., 1997, Critical Reviews in Food Science and Nutrition, 37: 705–718; Yang et al., 1997, Carcinogenesis, 18: 2361–2365). These prior art references disclose the chemistry of polyphenolic compounds isolated from tea. Some of these compounds contain benzotropolone moiety.

The present inventors have sought to discover pharmaceutical preparations having antioxidant and anti-inflammatory activity, and to identify essential agent(s) for treating inflammatory conditions. The present inventors have found that the compounds of the present invention having benzotropolone as a common moiety possess anti-inflammatory activity and that the compounds of the present invention can be prepared by employing simple and unique methods of synthesis.

SUMMARY OF THE INVENTION

The present invention provides therapeutic and preventive agents for scavenging free radicals and for inflammatory conditions, which show a high safety even in a long-term administration and are able to be utilized as part of food, beverage and/or cosmetic products that are used daily.

In its general aspect, the present invention discloses various compounds having a benzotropolone moiety within their structure and are capable of exhibiting potent anti-inflammatory action. Further, it has been surprisingly discovered that substantially pure compounds in high yields can be synthesized by oxidative coupling of a molecule containing pyrogallol unit (such as epigallocatechin or epigallocatechin gallate) and a molecule containing a catechol unit (such as epicatechin or epicatechin gallate) by using a peroxidase in the presence of $H_2O_2$.

In specific aspects, the present invention discloses benzotropolone-containing compounds and benzotropolone derivatives represented by the general formula:

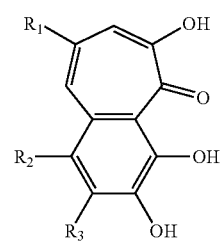

In the context of the present invention, the term "benzotropolone containing compound(s)" refers to a broad category of compounds, i.e., those already known in the art and those that are not known in the art. The term "benzotropolone derivative(s)" as used herein refers only to those novel compounds disclosed herein and/or that are not known in the art, which compounds can be made by those skilled in the art having the benefit of the present disclosure. Thus, benzotropolone derivatives are a subset of the broad class of compounds contemplated in the present invention.

In one embodiment, the present invention provides a composition, which is useful for modulating inflammatory conditions and/or use as an antioxidant in a mammal, having one or more benzotropolone derivatives and optionally a carrier, diluent or excipient. The benzotropolone containing compounds of the present invention can be those extracted from natural products or prepared synthetically and the composition can have a pharmaceutical ingredient or a nutraceutical ingredient or a combination of these ingredients as bioactive ingredients for modulating inflammatory conditions and/or use as an antioxidant in a mammal.

In another embodiment, a method of treating or reducing the progression of an inflammatory condition in a mammal by administering a composition having benzotropolone containing compound (s) is provided.

The benzotropolone containing compounds of the present invention can be made in forms suitable for oral delivery or non-oral deliveries such as, for example, topical administration. In case of oral administration, the benzotropolone containing compounds of the present invention can be administered to keep blood concentration sufficient enough to allow the manifestation of pharmacological effect, and the number of oral administration per day can be set as desired, particularly in light of the fact that the compounds of the present invention show minimal toxicity, if any.

In yet another embodiment, a simple, easy to control and reproducible method for synthesizing a benzotropolone derivative is provided. The synthesis involves, among other things, reacting a molecule comprising a pyrogallol unit with a molecule comprising a catechol unit in the presence of a peroxidase and $H_2O_2$.

DETAILED DESCRIPTION OF THE PREFERRED EMBODIMENTS

In one aspect of the invention, the present invention is directed to compositions having benzotropolone containing compounds (i.e., compounds with benzotropolone ring structures). Benzotropolone is a common moiety of numerous natural products. For example, theaflavins found in tea contain benzotropolone nucleus. The four major theaflavins that can be obtained from black tea are theaflavin, theaflavin-3-gallate, theaflavin-3'-gallate, theaflavin-3,3'-digallate. The other benzotropolone containing compounds that can be obtained from black tea are epitheaflavic acid, epitheaflavic acid-3'-O-gallate, isotheaflavin, theaflavate A, theaflavate B, isotheaflavin-3'-O-gallate and neotheaflavin-3-O-gallate.

Theaflavins can be produced by enzymatic oxidation of their parent flavonols, i.e., a catechol or di-hydroxylated B ring unit and a pyrogallol or tri-hydroxylated B ring unit to their quinones, and followed by their condensation. Theaflavin, for example, is a chemical compound that is the oxidation and condensation product of (−)-epicatechin and (−)-epigallocatechin. Listed in table 1 below are the parent flavonols of some of the benzotropolone containing compounds of the present invention.

TABLE 1

Parent flavonols of theaflavins and epitheaflavic acids

| Theaflavins | Parent flavonols |
|---|---|
| Theaflavin | (−)-epicatechin (EC) and (−)-epigallocatechin (EGC) |
| Theaflavin-3-gallate | (−)-epicatechin and (−)-epigallocatechin gallate (EGCG) |
| Theaflavin-3'-gallate | (−)-epicatechin gallate (ECG) and (−)-epigallocatechin |
| Theaflavin-3,3'-digallate | (−)-epicatechin gallate and (−)-epigallocatechin gallate |
| Epitheaflavic acid | (−)-epicatechin and gallic acid (GA) |
| Epitheaflavic acid gallate | (−)-epicatechin gallate and gallic acid |

The benzotropolone containing compounds of the invention are those isolated from tea extracts and/or those synthesized by chemical oxidation of specific precursor compounds such as pyrogallol unit containing molecules and catechol unit containing molecules.

The preferred benzotropolone containing compounds that are useful and specifically contemplated in the present invention are:

Group 1: Theaflavins (general structures of black tea theaflavins): compounds #1, 2, 3, 4, 5, 6
1. Theaflavin
2. Theaflavin 3-gallate
3. Theaflavin 3'-gallate
4. Theaflavin 3,3'-digallate
5. Neotheaflavin
6. Neotheaflavin 3-gallate

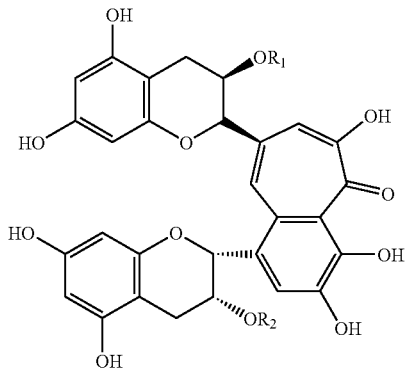

(EC, EGC) Theaflavin: $R_1 = R_2 = H$
(EC, EGC) Theaflavin-3-gallate: $R_1$ = galloyl; $R_2 = H$
(EGC, ECG) Theaflavin-3'-gallate; $R_1 = H$; $R_2$ - galloyl
(ECG, EGCG) Theaflavin-3-3'-digallate: $R_1 = R_2$ = galloyl

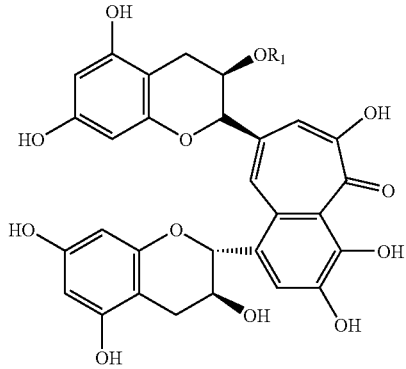

(C, EGC) Neo Theaflavin: R = H
(C, EGCG) Neo Theaflavin-3-gallate: R = galloy

Group 2: Theaflavate (benzotropolone structure contains an ester group): Compounds #7, 8, 9

7. Theaflavate A
8. Theaflavate B
9. Neotheaflavate B

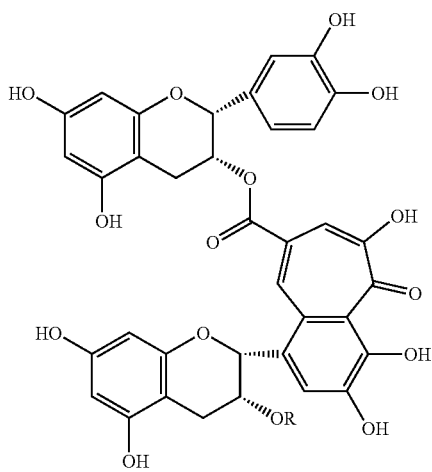

(ECG) Theaflavate A: R = gallate
(EC, ECG) Theaflavate B: R = H

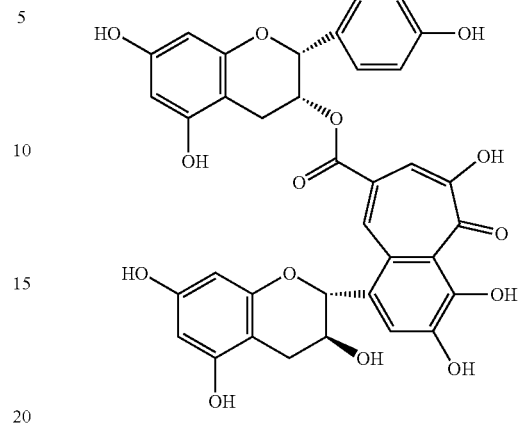

(C, ECG) Neo Theaflavate B

Group 3: Theaflavic acid (benzotropolone structure contains a carboxylic group): Compounds # 10, 11, 12, 17
   10. Theaflavic acid (CGA)
   11. Epitheaflavic acid
   12. Epitheaflavic acid 3-gallate
   17. Purpurogallin carboxylic acid

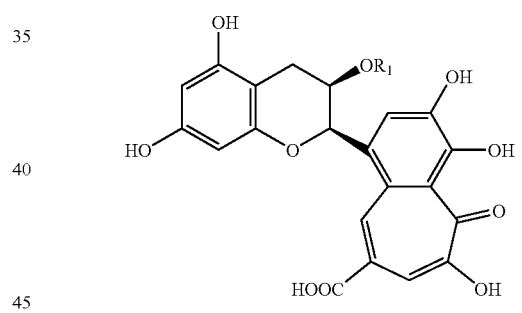

(EC, Gallic acid) Epitheaflavic acid: R = H
(ECG, Gallic acid) Epitheaflavic acid-3'-gallate: R = galloyl

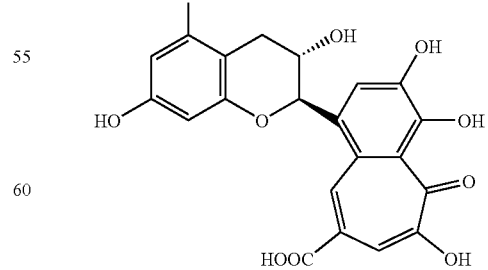

(C, Gallic acid) Theaflavic acid

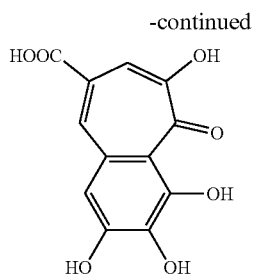

(Gallic acid) Purpurogallin carboxylic acid

Group 4: Catechol derived benzotropolones: Compounds #13, 14, 15, 16
13. EGCCa
14. EGCGCa
15. GACa
16. Purpurogallin

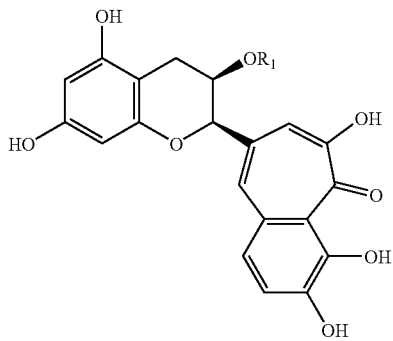

(Catechol, EGC) EGCCa: R = H
(Catechol, EGCG) EGCGCa: R = gallate

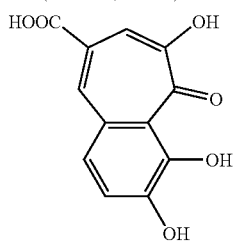

(Catechol, Gallic acid) GACa

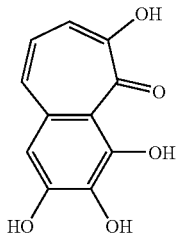

(Pyrogallol) Purpurogallin

Group 5: Interaction products of pyrogallol and tea catechins, catechol and caffeic acid: Compounds 18, 19, 20, 21, 22

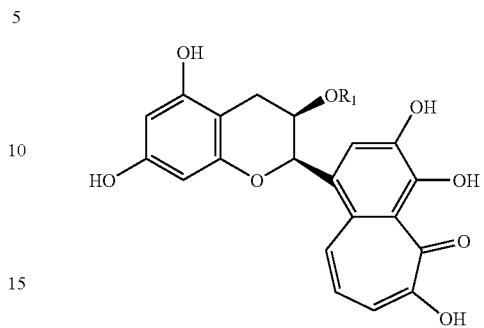

(EC, Pyrogallol) 18: R = H
(ECG, Pyrogallol) 19: R = galloyl

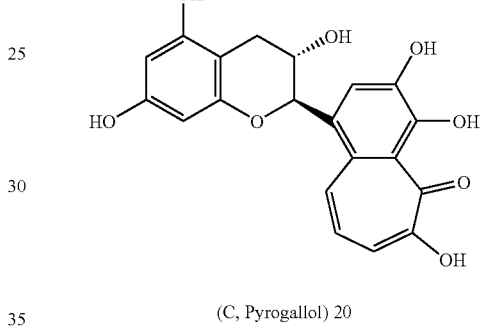

(C, Pyrogallol) 20

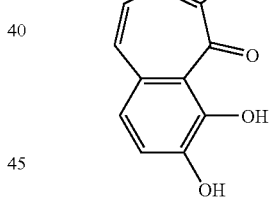
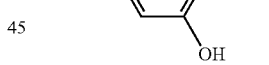

(Catechol, Pyrogallol) 21

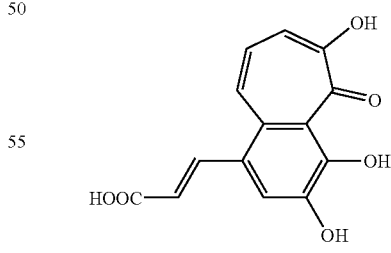

(Caffeic acid, Pyrogallol) 22

Group 6: Interaction products of chlorogenic acid or caffeic acid and catechins: Compounds 23, 24, 25, 26, 27, 28, 29, 30, 31, 32, 33

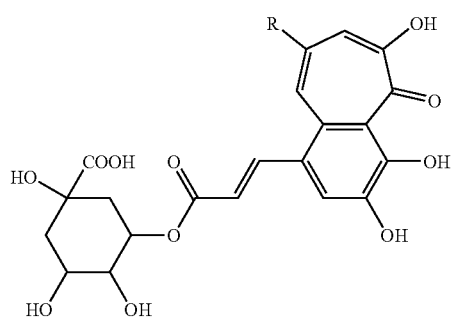

(Chlorogenic acid, Pyrogallol) 23: R═H
(Chlorogenic acid, Garlic acid) 24: R═COOH

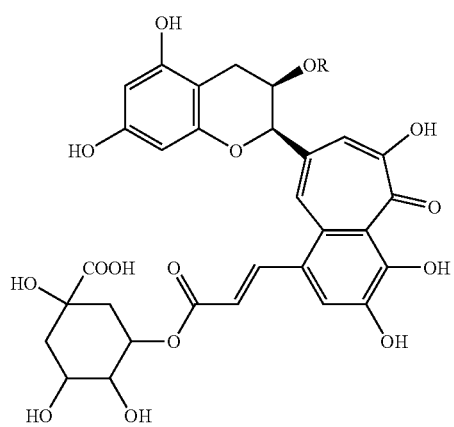

(Chlorogenic acid, EGC) 25: R═H
(Chlorogenic acid, EGCG) 26: R═galloyl

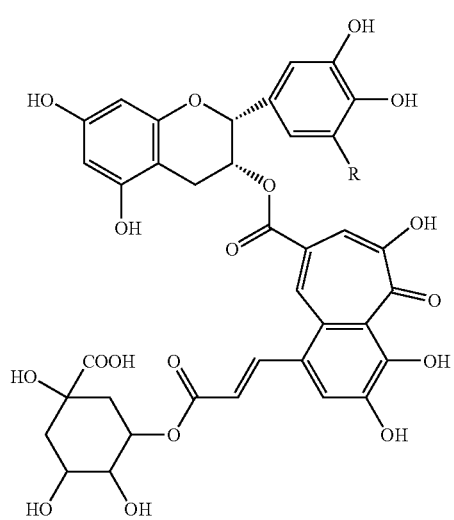

(Chlorogenic acid, ECG) 27: R═H
(Chlorogenic acid, EGCG) 28: R═OH

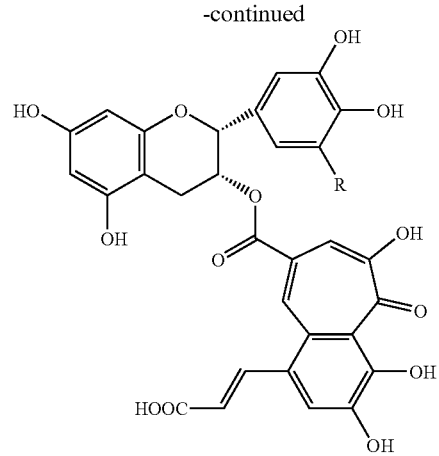

(Caffeic acid, ECG) 29: R═H
(Caffeic acid, EGCG) 30: R═OH

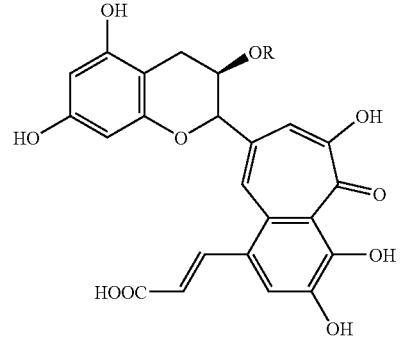

(Caffeic acid, EGC) 31: R═H
(Caffeic acid, EGCG) 32: R═galloyl

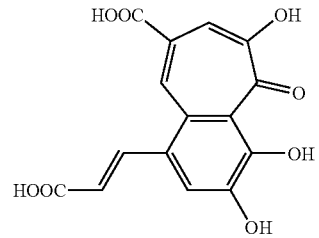

(Caffeic acid, Garlic acid) 33

Group 7: Derivatives of purpurogallin, purpurogallin carboxylic acid and GACa or other benzotropolone molecules (H of OH group replaced with acetate, methyl, ethyl, propyl or higher alkyl groups), such as: Compounds 34, 35 and 36

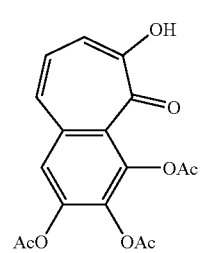

34

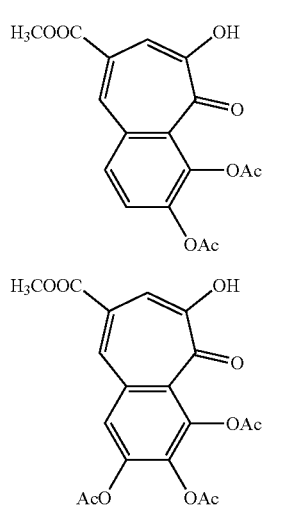

Of the above listed compounds, some compounds are already known to one skilled in the art as they have already been reported in the literature and some are novel and not known to one skilled in the art. For example, compound 9 (group 2) or compound 14 (group 4) or compounds listed under group 5 through group 7 are novel.

In another aspect, the present invention is directed to a unique, simple, easy control and reproducible manufacturing process that can enable efficient production of substantially pure benzotropolone containing compounds in high yields. For example, the theaflavins yields at least matching those obtained with prior art known methods have been achieved in accordance with the method of the invention in its simplest form. Specifically, for example, in the case of theaflavin 3-gallate, when the starting materials (parent flavonols) are one gram each (EC and EGCG, 1 g each), theaflavin 3-gallate yields of at least 0.2 g are achievable by the present method. The process involves a peroxidase catalyzed coupling of pyrogallol unit containing molecule(s) and/or catechol unit containing molecule(s) in the presence of $H_2O_2$.

For example, to prepare compounds 1 through 17 under groups 1–4 above in accordance with the methods of the present invention, parent flavonols are dissolved in a suitable buffer containing a peroxidase enzyme. The enzyme substrate, $H_2O_2$ is added to the mixture and the reaction mixture is extracted by a suitable solvent. The extract is subjected to column separation and eluted with a suitable solvent system to obtain benzotropolone containing compounds in high yields. The specific details about the synthesis of these compounds have been provided elsewhere in the specification. Based on these examples one skilled in the art would know how to choose the parent compounds (or parent flavonols) and suitable reagents and conditions in order to synthesize various benotropolone containing compounds or benotropolone derivatives of the invention.

For example, to prepare compounds 18–23 listed above, the following method can be used: First, the appropriate parent flavonol(s) is dissolved in a mixture of acetone-pH 5.0 phosphate citrate buffer (1:10, v/v, 50 mL), containing horseradish peroxidase and 1.0 ml of 3.13% $H_2O_2$. Then, while being stirred, an ice-cooled solution of pyrogallol in $H_2O$ is added in drops for about 45 minutes. The reaction mixture is extracted by ethyl acetate (50 ml×3). After concentration, the residue is subjected to Sephadex LH 20 column and eluted with acetone-water solvent system (40%). The appropriate parent compound in each case is as follows: EC (for compound 18), ECG (for compound 19), cateching (for compound 20), catechol (for compound 21); caffeic acid (for compound 22) and chlorogenic acid (for compound 23)

Likewise, for example, to prepare compounds 24–33 listed above, the following method can be used: First, appropriate parent flavonols are dissolved in a mixture of acetone-pH 5.0 phosphate citrate buffer (1:10, v/v, 50 mL) containing horseradish peroxidase. Then, while being stirred, 2.0 ml of 3.13% $H_2O_2$ is added four times during 45 minutes. The reaction mixture is extracted by ethyl acetate (50 ml×3). After concentration, the residue is subjected to Sephadex LH 20 column eluted with acetone-water solvent system (40%).

The appropriate parent compounds in each case are as follows: Chlorogenic acid and Garlic acid (for compound 24), Chlorogenic acid and EGC (for compound 25), Chlorogenic acid and EGCG (for compound 26), Chlorogenic acid and ECG (for compound 27); Chlorogenic acid and EGCG (for compound 28) and Caffeic acid and ECG (for compound 29) Caffeic acid and EGCG (for compound 30), Caffeic acid and EGC (for compound 31), Caffeic acid and EGCG (for compound 32), Caffeic acid and Garlic acid (for compound 33).

To prepare compound 34 listed above, first, Purpurogallin is reacted with acetic anhydride in pyridine at room temperature for overnight. Then, after evaporation of the solvent in vacuo, the residue is applied to Sephadex LH 20 column eluted with acetone-water solvent system (40%) to obtain the compound.

To prepare compound 35 listed above, first, a solution of GACa in methanol is acidified with concentrated hydrochloric acid. Then, the mixture is stirred and heated to reflux for 30 min and then extracted with ethyl acetate. After evaporation, the residue is reacted with acetic anhydride in pyridine at room temperature for overnight. After evaporation of the solvent in vacuo, the residue is applied to Sephadex LH 20 column eluted with acetone-water solvent system (40%) to obtain the compound.

To prepare compound 36 listed above, first, a solution of Purpurogallin in methanol is acidified with concentrated hydrochloric acid. Then, the mixture is stirred and heated to reflux for 30 min and then extracted with ethyl acetate. After evaporation, the residue is reacted with acetic anhydride in pyridine at room temperature for overnight. After evaporation of the solvent in vacuo, the residue is applied to Sephadex LH 20 column eluted with acetone-water solvent system (40%) to obtain the compound.

In an aspect of the present invention, compositions having a pharmaceutical or a nutraceutical agent useful for the treatment or prevention of an ailment or a symptom thereof (e.g., inflammation), are disclosed. The composition of the present invention may also be used as antioxidants. The pharmaceutical or a nutraceutical agent in the composition includes at least one benozotropolone compound or derivative thereof as a biologically active agent. The composition may be formulated into liquid, solid or powder forms and administered to a mammal, including humans, in need thereof.

A pharmaceutical, as used herein, is a synthetically produced bioactive compound, where no structurally identical and naturally produced analog to the synthetically produced bioactive compound exists. Alternatively, a pharmaceutical is a biologically active compound derived from natural sources (e.g., plants and plant products) but is not a food item, or a food additive or a dietary supplement. Nutraceutical as contemplated herein refers to a food item, or a food additive or a dietary supplement that offers ameliorative health or medical effects, including prevention and/or treatment of disease. A dietary supplement is one which is used to supplement one or more dietary (food) ingredients such as minerals, vitamins, herbs, or herbal extract, carbohydrate, a fat, a protein or combinations of these ingredients.

In addition to the benozotropolone compound or derivative thereof as a biologically active compound in the composition, a pharmaceutical or a nutraceutical agent used in the composition of the present invention may further include conventionally used compounds (e.g., ibuprofen, aspirin, NSAIDS, vitamin E, and/or orange peel extract or other herbal extracts; See, WO 01/21137 the contents of which are incorporated herein by reference) for the treatment or prevention of a given ailment. Further, the pharmaceutical and nutraceutical used in the present invention include the equivalent salts of the benzotropolone containing compounds, which achieve substantially the same effect as the pharmaceutical or the nutraceutical. In an embodiment of the invention, use of a nutraceutical agent in the composition may be optional to improve the efficacy of a pharmaceutical agent in the composition for the treatment or prevention of the given ailment. Likewise, use of a pharmaceutical agent in the composition may be optional to improve the efficacy of a nutraceutical agent in the composition for the treatment or prevention of the given ailment. Alternatively, the pharmaceutical and nutraceutical may be combined and processed into a suitable formulation.

As already noted, the composition of the present invention includes an effective amount of at least one benzotropolone compound or derivative thereof as a biologically active agent. In an embodiment, more than one benzotropolone compound or derivative thereof is used in the composition. They may be present in amounts ranging from none to all of the effective amount or to amounts less than all of the effective proportion or amount, provided that at least one benzotropolone compound or derivative thereof is present in an amount effective to treat or prevent inflammatory condition. For example, a composition may have an effective amount of EC, Pyrogallol (i.e., compound 18 disclosed above) as a benzotropolone containing compound or derivative. In addition, for example, the composition may have neotheaflavate B and/or EGCGCa as additional benzotropolone containing compounds or derivatives. The additional benzotropolone containing compounds or derivatives may be present from none to a fraction or all of an amount effective as anti-inflammatory compounds or antioxidants. While, the presence of additional benzotropolone containing compounds do not affect the effectiveness of the composition, these may improve (or synergistic to) the efficacy of a benzotropolone containing compounds or derivatives in the composition.

In another aspect, the present invention also discloses antioxidant activities of the compositions having benzotropolone containing compounds disclosed herein. Oxygen radical absorbence capacity (ORAC) assay, which is a measure of free radical scavenging ability, is simple and sensitive method to measure the oxygen-radical absorbing capacity. It has been widely used for measuring the antioxidant activity of food and nutraceutical components. ORAC assay was developed by Cao et al., 1993, Free Radical Biol. Med. 14:303–311. In the assay, β-phycoerythrin (β-PE) was used as fluorescent indicator protein and 2,2'-Azobis(2-amidinopropane) dihydrochloride (AAPH) used as a peroxy radical generator. β-PE is a photosynthetic protein found in red algae. β-PE has been used as fluorescent probe because of its distinct excitation and emission wavelength (Ex. 540 nm, Em. 565 nm). The use of β-PE as a fluorescent probe, however, has certain defects. When reactive oxygen species attack the β-PE, it can easily lose the fluorescence. Furthermore, the ORAC value can be affected by possible interaction between polyphenols and proteins. Recently, Ou et al., 2001, J. Agric. Food Chem. 49:4619–4626 reported an improved ORAC method using fluorescein, instead of β-PE, as a fluorescent probe. Accordingly, fluorescein is used as a fluorescent probe in ORAC assays for testing the antioxidant activities of the compounds of the present invention.

In yet another aspect of the invention, the present invention is directed to a method of preventing and/or treating inflammation in an animal using compositions having benzotropolone containing compounds disclosed herein. A number of studies revealed that green tea and black tea polyphenols have anti-inflammatory activity along with considerable amount of epidemiological evidence. The anti-inflammatory activity (or anti-edema) of benzotropolone containing compounds of the present invention can be tested using 12–0-tetradecanoylphorbol- 13-acetate (TPA) TPA-induced inflammatory skin edema assay. Application of TPA on skin results in induction of omithine decarboxylase activity that increases the polyamine level and epidermal hyperplasia, and inflammation, and pro-inflammatory cytokine (e.g., IL-1β) and prostaglandins (prostaglandin $E_2$) production at the site. The benzotropolone containing compounds can be applied either prior to or subsequent to or simultaneously with the topical application of TPA to skin tissue (e.g. mice ear).

Indeed, the inhibitory effects of some black tea polyphenols, including theaflavin, a mixture of theafavin-3-gallate and theaflavin-3'-gallate, theaflavin-3,3'-digallate, and the green tea polyphenol (−)-epigallocatechin-3-gallate (EGCG) on 12-O-tetradecanoylphorbol-13-acetate (TPA)-induced edema and omithine decarboxylase (ODC) activity was recently studied (Liang et al. 2002, Nutrition and Cancer 42(2): 217–223). Topical application of these polyphenols onto experimental mice resulted in inhibition of TPA-induced ear edema and skin epidermal ODC activity.

To explain the structure-activity relationship of three theaflavins and anti-inflammatory activity, there are two possibilities that are commonly accepted in the field.

(a) Since TF-3 molecule has 13 OH (phenolic) groups, TF-2 has 10 OH groups and TF-1 has 7 OH groups, it is therefore the more OH group the stronger the anti-inflammatory activity.

(b) Since TF-3 contains two gallate groups, TF-2 contains one gallate group and TF-1 contain no gallate, it is therefore the more gallate group the stronger anti-inflammatory activity.

The present inventors have, however, unexpectedly found that this explanation is incorrect, and that it is the presence of benzotropolone unit or moiety that is important, which may even be for conferring the anti-inflammatory property. For example, it has been found that there is no relationship between the number of OH group and anti-inflammatory activity. Many compounds that have no gallic group such as EGCCa showed comparable activity to theaflavin monogallates. See Example V below. Of the anti-inflammatory agents of the present invention, benzotropolone derivatives are preferred.

The compositions useful in the context of the present inventive method can be administered to an animal, especially a mammal, and preferably a human, by any suitable means or routes. Oral administration is preferred, but other routes of administration such as parenteral and topical administration can be used. The compounds of the present invention can be administered alone or they can be mixed with a pharmaceutically acceptable carrier or diluent depending on the mode of administration. For oral administration, for example, the compounds of this invention can be administered in its pure form as powders or administered in the form of tablets, capsules, lozenges, syrups, elixirs, solutions, suspensions and the like, in accordance with the standard pharmaceutical practice.

The effectiveness of the compositions having compounds and derivatives of the present invention, whether by oral or topical delivery, has been shown herein by using an art recognized animal model system (Sala et al., 2003, European Journal of Pharmacology 461(1): 53–61; Ukiya et al., 2001, Journal of Agricultural and Food Chemistry 49(7): 3187–3197; Huang et al., 2003, Protective effect of dibenzoylmethane on chemically- and UV light-induced skin, inflammation, sunburn lesions, and skin carcinogenesis in mice, In: Food Factors in Health Promotion and Disease Prevention, F. Shahidi, C.-T. Ho, S. Watanabe and T. Osawa. Washington, D.C, American Chemical Society: 196–207; Huang et al., 1988, Cancer Research. 48: 5941–5946. See, details relating to anti-inflammatory activity of benzotropolone containing compounds disclosed under the Examples section below. As can be seen from the working examples, the benzotropolone containing compounds of the present invention are indeed effective in vivo.

The daily dose of benzotropolone compound(s) or derivative(s) can be appropriately determined and is not particularly limited. In most instances, however, an effective dosage for a patient in need of the treatment will be between 0.1 mg/kg to 300 mg/kg body weight daily. In any case, the active compounds of this invention are administered at a therapeutically effective amount to achieve the desired therapeutic effect without causing any serious adverse effects in the patient treated. The therapeutically effective amount for each active compound can vary with factors including but not limited to the activity of the compound used, the severity of the conditions to be alleviated, the total weight of the patient treated, the route of administration, the age and sensitivity of the patient to be treated, and the like, as will be apparent to a skilled artisan. The amount of administration is adjusted as the various factors change over time.

EXAMPLE(S)

The following examples further illustrate the present invention. The examples below are carried out using standard techniques, that are well known and routine to those of skill in the art, except where otherwise described in detail. The examples are illustrative and do not limit the invention.

I. Synthesis of Theaflavin Mixtures

A mixture of theaflavins were synthesized from their parent flavonols using enzymatic oxidation methods.

Specifically, after filtration, the crude green tea polyphenol (1.8 g, commercial sample containing 80% catechins) was loaded directly onto a Sephadex LH-20 column eluted first with 95% ethanol to remove non-catechin flavonoids, then the column was eluted with acetone to obtain a mixture of tea catechins (1.34 g). The tea catechins were dissolved in pH-5 buffer (50 mL), which contained 4 mg horseradish peroxidase. While being stirred, 3.0 mL of 3.13% $H_2O_2$ was added 5 times during 1 hr. The enzymatic reaction solution containing catechins and crude peroxidase had turned into a reddish solution during oxidation reaction. The reaction mixture was extracted by ethyl acetate (50 mL×3). After concentration, the residue (0.97 g) was subjected to Sephadex LH 20 column eluted with acetone-water solvent system (from 35% to 50%). 350 mg of a theaflavin mixture was obtained.

II. Preparation of Tea Catechins

After filtration, the crude green tea polyphenol (10 g) was loaded directly onto a Sephadex LH-20 column eluted with 95% ethanol to give three catechins, namely epicatechin gallate (ECG), epigallocatechin (EGC) and epigallocatecin gallate (EGCG). Each catechin was further purified through RP C-18 column eluted with Methanol-Water solvent system.

III. Synthesis of Pure Benzotropolone Containing Compounds

Various benzotropolone containing compounds were synthesized by enzymatic oxidative coupling of a molecule containing pyrogallol unit (such as epigallocatechin) and a molecule containing catechol unit (such as epicatechin) by using horseradish peroxidase (in the presence of $H_2O_2$) or polyhenol oxidase.

The following analytical procedures were used: Thin-layer chromatography was performed on Sigma-Aldrich silica gel TLC plates (250 μm thickness, 2–25 μm particle size), and the spots were detected by UV illumination, and spraying with 5% (v/v) $H_2SO_4$ in an ethanol solution. $^1H$ NMR spectra were obtained on a Varian 600 instrument (Varian Inc., Palo Alto, Calif.). The compound was analyzed in $CH_3OH$-$d_4$, with TMS as internal standard. APCI-Mass spectra were recorded on a Micromass Platform II system (Micromass Co., Beverly, Mass.) equipped with a Digital DECPC XL 560 computer for data analysis.

A. Synthesis of Benzotropolone Containing Compounds Catalyzed by Peroxidase

The following seventeen benzotropone containing compounds were synthesized by the reaction of a molecule containing pyrogallol unit and a molecule containing catechol unit catalyzed by horseradish peroxidase in the presence of $H_2O_2$.

1. Theaflavin

EC (1 g) and EGC (1 g) were dissolved in a mixture of acetone-pH 5.0 phosphate citrate buffer (1:10, v/v, 50 mL) which contained 4 mg horseradish peroxidase. While being stirred, 2.0 ml of 3.13% $H_2O_2$ was added four times during 45 minutes. The reaction mixture was extracted by ethyl acetate (50 ml×3). After concentration, the residue was subjected to Sephadex LH 20 column eluted with acetone-water solvent system (40%). 250 mg theaflavin was obtained.

$^1H$ NMR ($CD_3OD$, 600 MHz): $\delta_H$ 7.97 1H s, 7.85 1H s, 7.34 1H s, 6.02 1H d, J=2.4 Hz, 5.99 1H d, J=2.4 Hz, 5.97 1H d, J=2.4 Hz, 5.96 1H d, J=2.4 Hz, 5.64 1H brs, 4.91 1H brs, 4.45 1H d, J=2.4 Hz, 4.32 1H brs, 2.98 1H dd, J=4.8, 16.8 Hz, 2.94 1H dd, J=4.8, 16.8, 2.84 1H brd, J=16.8 Hz, 2.82 1H brd, J=16.8 Hz; $^{13}C$ NMR ($CD_3OD$, 150 MHz): $\delta_C$ 185.1, 158.1, 158.0, 157.6, 157.5, 157.3, 156.6, 155.1, 150.9, 146.1, 134.4, 131.2, 129.0, 126.6, 123.7, 121.9, 118.3, 100.3, 99.8, 96.8, 96.1, 96.0, 81.2, 77.1, 66.7, 65.6, 30.0, 29.4 ppm.

2. Theaflavin 3-gallate

EC (1 g) and EGCG (1 g) were dissolved in a mixture of acetone-pH 5.0 phosphate citrate buffer (1:10, v/v, 50 mL), which contained 4 mg horseradish peroxidase. While being stirred, 2.0 ml of 3.13% $H_2O_2$ was added four times during 45 minutes. The reaction mixture was extracted by ethyl acetate (50 ml×3). After concentration, the residue was subjected to Sephadex LH 20 column eluted with acetone-water solvent system (45%). 220 mg theaflavin 3-gallate was obtained.

$^1$H NMR (CD$_3$OD, 600 MHz): $\delta_H$ 7.91 1H s, 7.80 1H s, 7.38 1H s, 6.80 2H s, 6.02 1H d, J=1.8 Hz, 6.00 1H d, J=2.4 Hz, 5.99 2H s, 5.78 1H brs, 5.55 1H brs, 5.11 1H s, 4.16 brd, J=2.4 Hz, 3.07 dd, J=4.8, 16.8 Hz, 2.99 dd, J=4.2, 16.8, 2.91 brd, J=16.8 Hz, 2.83 brd, J=16.8 Hz; $^{13}$C NMR (CD$_3$OD, 150 MHz): $\delta_C$ 185.6, 167.4, 158.0, 157.9, 157.8, 157.3, 156.4, 156.3, 155.4, 151.2, 146.4, 146.3, 139.9, 133.5, 131.3, 128.7, 125.7, 123.8, 121.9, 121.0, 117.0, 110.1, 100.2, 99.3, 96.9, 96.8, 96.2, 95.8, 79.8, 77.0, 69.0, 65.7, 30.1, 27.1 ppm.

3. Theaflavin 3'-gallate

ECG (1 g) and EGC (1 g) were dissolved in a mixture of acetone-pH 5.0 phosphate citrate buffer (1:10, v/v, 50 mL), which contained 4 mg horseradish peroxidase. While being stirred, 2.0 ml of 3.13% $H_2O_2$ was added four times during 45 minutes. The reaction mixture was extracted by ethyl acetate (50 ml×3). After concentration, the residue was subjected to Sephadex LH 20 column eluted with acetone-water solvent system (45%). 110 mg theaflavin 3'-gallate was obtained.

$^1$H NMR (CD$_3$OD, 600 MHz): $\delta_H$ 7.88 1H s, 7.87 1H s, 7.37 1H s, 6.84 2H s, 6.06 d, J=2.4 Hz, 6.00 1H d, J=2.4 Hz, 5.98 1H d, J=2.4 Hz, 5.97 d, J=2.4 Hz, 5.87 brs, 5.81 1H brd J=3.0 Hz, 4.94 1H brs, 4.33 1H brs, 3.09 1H dd, J=4.8, 17.4 Hz, 2.96 1H dd, J=4.8, 16.8, 2.88 1H brd, J=17.4 Hz, 2.86 dd, J=2.4, 16.8 Hz; $^{13}$C NMR (CD$_3$OD, 150 MHz): $\delta_C$ 185.6, 167.2, 158.0, 157.9, 157.8, 157.7, 157.0, 156.6, 156.0, 155.5, 151.1, 146.2, 139.7, 134.8, 130.3, 128.8, 125.9, 123.0, 121.9, 120.9, 118.3, 99.8, 99.6, 96.8, 96.7, 95.8, 95.7, 81.2, 75.8, 68.3, 66.5, 29.3, 27.2 ppm.

4. Theaflavin 3,3'-digallate

ECG (1 g) and EGCG (1 g) were dissolved in a mixture of acetone-pH 5.0 phosphate citrate buffer (1:10, v/v, 50 mL), which contained 4 mg horseradish peroxidase. While being stirred, 2.0 ml of 3.13% $H_2O_2$ was added four times during 45 minutes. The reaction mixture was extracted by ethyl acetate (50 ml×3). After concentration, the residue was subjected to Sephadex LH 20 column eluted with acetone-water solvent system (45%). 100 mg theaflavin 3,3'-digallate was obtained.

$^1$H NMR (CD$_3$OD, 600 MHz): $\delta_H$ 7.79 1H s, 7.76 1H s, 7.47 1H s, 6.88 2H s, 6.80 2H s, 6.07 1H d, J=2.4 Hz, 6.03 2H d, J=2.4 Hz, 6.00 1H d, J=2.4 Hz, 5.86 1H brs, 5.76 1H m, 5.67 1H m, 5.21 1H s, 3.17 1H dd, J=4.8, 16.8 Hz, 3.09 1H dd, J=4.8, 17.4, 2.91 2H m.

5. Neotheaflavin

C (catechin) (0.8 g) and EGC (0.8 g) were dissolved in a mixture of acetone-pH 5.0 phosphate citrate buffer (1:10, v/v, 50 mL), which contained 4 mg horseradish peroxidase. While being stirred, 2.0 mL of 3.13% $H_2O_2$ was added four times during 45 minutes. The reaction mixture was extracted by ethyl acetate (50 mL×3). After concentration, the residue was subjected to Sephadex LH 20 column eluted with acetone-water solvent system (45%). 120 mg neotheaflavin was obtained.

$^1$H NMR ((CD$_3$)$_2$CO, 600 MHz): $\delta_H$ 8.26 1H s, 7.46 1H s, 7.63 1H s, 6.06 d, J=2.4 Hz, 6.03 d, J=2.4 Hz, 5.96 d, J=2.4 Hz, 5.95 d, J=2.4 Hz, 5.62 d, J=7.8 Hz, 5.01 1H m, 4.39 1H m, 4.15 1H m, 2.97 dd, J=5.4, 15.6 Hz, 2.91 dd, J=4.2, 16.8, 2.84 dd, J=1.2, 16.8 Hz, 2.66 dd, J=9.6, 15.6 Hz; $^{13}$C NMR ((CD$_3$)$_2$CO, 150 MHz): $\delta_C$ 184.8, 157.6, 157.5, 157.4, 157.0, 156.7, 156.6, 154.4, 150.5, 146.2, 134.8, 132.2, 130.8, 128.6, 122.3, 121.6, 119.2, 100.7, 99.2, 96.4, 96.3, 95.6, 95.4, 81.5, 79.1, 69.5, 66.6, 30.0, 29.3 ppm.

6. Neotheaflavin 3-gallate

C (1 g) and EGCG (1 g) were dissolved in a mixture of acetone-pH 5.0 phosphate citrate buffer (1:10, v/v, 50 mL), which contained 4 mg horseradish peroxidase. While being stirred, 2.0 ml of 3.13% $H_2O_2$ was added four times during 45 minutes. The reaction mixture was extracted by ethyl acetate (50 mL×3). After concentration, the residue was subjected to Sephadex LH 20 column eluted with acetone-water solvent system (45%). 170 mg neotheaflavin 3-gallate was obtained.

$^1$H NMR (CD$_3$OD, 600 MHz): $\delta_H$ 8.04 1H s, 7.59 1H s, 7.49 1H s, 6.92 2H s, 6.01 2H d, J=2.4 Hz, 5.98 1H d, J=2.4 Hz, 5.97 1H d, J=2.4 Hz, 5.67 1H brs, 5.56 1H brd, J=6.6 Hz, 5.11 1H s, 4.22 1H m, 3.03 1H dd, J=4.8, 17.4 Hz, 2.92 1H brd, J=16.8 Hz, 2.83 1H dd, J=4.8, 16.8, 2.66 dd, J=8.4, 16.8; $^{13}$C NMR (CD$_3$OD, 150 MHz): $\delta_C$ 185.8, 167.4, 158.0, 157.9, 157.8, 156.7, 156.5, 155.3, 151.6, 146.9, 146.2, 139.9, 134.0, 132.0, 130.4, 127.7, 122.3, 121.0, 117.6, 110.2, 100.6, 99.2, 96.9, 96.7, 95.9, 95.6, 80.5, 77.1, 69.9, 68.8, 28.5, 27.0 ppm.

7. Theaflavate A

ECG (0.85 g) was dissolved in pH 5 buffer (1:10, v/v, 50 mL), which contained 2 mg horseradish peroxidase. While being stirred, 1.5 mL of 3.13% $H_2O_2$ was added three times during 30 minutes. The reaction mixture was extracted by ethyl acetate (50 mL×3). After concentration, the residue was subjected to Sephadex LH 20 column eluted with acetone-water solvent system (45%). 60 mg theaflavate A was obtained and 600 mg ECG was recovered.

$^1$H NMR (CD$_3$OD, 600 MHz): $\delta_H$ 8.33 1H s, 7.81 1H s, 7.65 1H s, 6.87 1H dd, J=1.8, 7.8 Hz, 6.85 1H d, J=1.8 Hz, 6.80 2H s, 6.53 1H d, J=7.8 Hz, 6.15 1H d, J=2.4 Hz, 6.11 1H d, J=2.4, 6.09 1H d, J=2.4 Hz, 5.98 1H, d, J=2.4 Hz, 5.69 1H brs, 5.64 1H brs, 5.52 1H, brd, J=3.6Hz, 5.11 1H s, 3.32 dd, J=4.8, 18.0Hz, 3.10 dd, J=4.8, 18.0Hz, 3.05 dd, J=1.8, 16.8 Hz, 2.91 d, J=16.8; $^{13}$C NMR (CD$_3$OD, 150 MHz): $\delta_C$ 186.8, 167.8, 167.3, 158.2, 158.1, 158.0, 157.9, 157.2, 157.1, 155.3, 149.5, 146.4, 146.3, 146.0, 140.0, 133.5, 131.2, 126.6, 124.8, 122.9, 122.6, 121.0, 119.0, 116.4, 115.8, 114.2, 110.2, 100.0, 99.4, 97.3, 97.2, 96.5, 96.4, 78.0, 75.6, 72.1, 68.9, 27.3, 26.7 ppm.

8. Theaflavate B

EC (0.5 g) and ECG (0.5 g) were dissolved in a mixture of acetone-pH 5.0 phosphate citrate buffer (1:10, v/v, 50 mL), which contained 2 mg horseradish peroxidase. While being stirred, 2.0 mL of 3.13% $H_2O_2$ was added four times during 45 minutes. The reaction mixture was extracted by ethyl acetate (50 mL×3). After concentration, the residue was subjected to Sephadex LH 20 column eluted with acetone-water solvent system (45%). 200 mg theaflavate B was obtained.

$^1$H NMR (CD$_3$OD, 600 MHz): $\delta_H$ 8.26 1H s, 7.88 1H s, 7.59 1H s, 6.87 1H dd, J=1.8, 7.8 Hz, 6.86 1H d, J=1.8 Hz, 6.55 1H d, J=7.8 Hz, 6.16 1H d, J=2.4 Hz, 6.08 1H d, J=2.4, 6.05 1H d, J=2.4 Hz, 5.98 1H, d, J=2.4 Hz, 5.66 1H brs, 5.46 1H brs, 5.08 1H s, 4.14 1H brs, 3.34 dd, J=4.8, 16.8 Hz, 3.21 dd, J=4.8, 16.8 Hz, 3.17 dd, J=3.6, 16.2 Hz, 2.88 d, J=16.8; $^{13}$C NMR (CD$_3$OD, 150 MHz): $\delta_C$ 186.4, 167.8, 158.3, 158.0, 157.9, 157.7, 157.4, 157.1, 154.9, 151.8, 149.5, 146.3, 146.0, 134.8, 132.3, 131.3, 126.5, 124.4, 123.7, 122.4, 119.2, 116.3, 115.8, 114.4, 100.7, 99.5, 97.2, 97.1, 96.6, 96.5, 78.1, 77.0, 72.1, 66.7, 30.0, 26.7 ppm.

9. Neotheaflavate B

C (0.5 g) and ECG (0.5 g) were dissolved in a mixture of acetone-pH 5.0 phosphate citrate buffer (1:10, v/v, 50 mL), which contained 2 mg horseradish peroxidase. While being stirred, 2.0 ml of 3.13% $H_2O_2$ was added four times during 45 minutes. The reaction mixture was extracted by ethyl acetate (50 ml×3). After concentration, the residue was subjected to Sephadex LH 20 column eluted with acetone-water solvent system (45%). 90 mg neotheaflavate B was obtained.

$^1$H NMR (CD$_3$OD, 600 MHz): $\delta_H$ 8.77 1H s, 7.64 1H s, 7.61 1H s, 6.88 1H d, J=1.8 Hz, 6.82 1H dd, J=1.8, 8.4 Hz, 6.64 1H d, J=8.4 Hz, 6.03 1H d, J=2.4 Hz, 5.98 1H d, J=2.4, 5.96 2H brs, 5.58 1H brs, 5.38 1H brd, J=7.2 Hz, 5.04 1H s, 4.07 1H m, 3.03 dd, J=4.8, 16.8 Hz, 2.95 brd, J=16.8, 2.91 dd, J=4.8, 16.8 Hz, 2.66 dd, J=3.6, 16.2 Hz; $^{13}$C NMR (CD$_3$OD, 150 MHz): $\delta_C$ 186.6, 167.7, 157.9, 157.7, 157.3, 157.0, 156.8, 154.7, 152.3, 149.8, 146.0, 145.8, 135.0, 134.3, 131.2, 128.8, 124.0, 122.5, 119.0, 116.2, 115.8, 114.4, 101.2, 99.2, 97.0, 96.8, 96.1, 95.9, 79.7, 78.0, 72.0, 69.6, 29.6, 26.6 ppm.

10. Theaflavic Acid (CGA)

C (0.5 g) and gallic acid (0.5 g) were dissolved in a mixture of acetone-pH 5.0 phosphate citrate buffer (1:10, v/v, 50 mL), which contained 2 mg horseradish peroxidase. While being stirred, 2.0 mL of 3.13% $H_2O_2$ was added four times during 45 minutes. The reaction mixture was extracted by ethyl acetate (50 mL×3). After concentration, the residue was subjected to Sephadex LH 20 column eluted with acetone-water solvent system (45%). 60 mg theaflavic acid and 20 mg purpurogallin carboxylic acid were obtained.

$^1$H NMR (CD$_3$OD, 600 MHz): $\delta_H$ 9.00 1H s, 7.82 1H s, 7.66 1H s, 5.98 1H d, J=2.4 Hz, 5.91 1H d, J=2.4, 5.43 1H brd, J=7.2 Hz, 4.21 1H, m, 2.94 dd, J=4.8, 16.2 Hz, 2.64 dd, J=4.8, 16.2 Hz; $^{13}$C NMR (CD$_3$OD, 150 MHz): $\delta_C$ 186.6, 170.3, 157.9, 157.6, 156.6, 154.7, 152.2, 149.3, 139.5, 134.4, 132.2, 128.9, 125.0, 122.7, 116.5, 100.7, 96.8, 96.1, 80.0, 69.1, 29.3 ppm.

11. Epitheaflavic Acid

Epicatechin (EC) (0.5 g) and gallic acid (1 g) were dissolved in a mixture of acetone-pH 5.0 phosphate citrate buffer (1:10, v/v, 50 mL), which contained 2 mg horseradish peroxidase. While being stirred, 2.0 mL of 3.13% $H_2O_2$ was added four times during 45 minutes. The reaction mixture was extracted by ethyl acetate (50 mL×3). After concentration, the residue was subjected to Sephadex LH 20 column eluted with acetone-water solvent system (45%). 70 mg epitheaflavic acid and 25 mg purpurogallin carboxylic acid were obtained.

$^1$H NMR (CD$_3$OD, 600 MHz): $\delta_H$ 8.60 1H s, 7.95 1H s, 7.80 1H s, 6.09 1H s, 6.00 1H s, 5.88 1H s, 5.77 1H m, 3.17 1H dd, J=4.8, 17.4 Hz, 2.94 1H d, J=17.4 Hz; $^{13}$C NMR (CD$_3$OD, 150 MHz): $\delta_C$ 186.5, 170.1, 158.2, 157.7, 157.2, 155.0, 151.6, 149.2, 134.2, 132.2, 126.7, 125.2, 123.4, 122.6, 116.2, 99.2, 96.8, 96.1, 77.0, 66.4, 30.0 ppm.

12. Epitheaflavic Acid 3-gallate

ECG (0.5 g) and gallic acid (1 g) were dissolved in a mixture of acetone-pH 5.0 phosphate citrate buffer (1:10, v/v, 50 mL), which contained 2 mg horseradish peroxidase. While being stirred, 2.0 mL of 3.13% $H_2O_2$ was added four times during 45 minutes. The reaction mixture was extracted by ethyl acetate (50 mL×3). After concentration, the residue was subjected to Sephadex LH 20 column eluted with acetone-water solvent system (45%). 20 mg epitheaflavic acid 3-gallate, 40 theaflavate A and 10 mg purpurogallin carboxylic acid were obtained.

$^1$H NMR (CD$_3$OD, 600 MHz): $\delta_H$ 8.64 1H s, 7.84 1H s, 7.83 1H s, 6.83 2H s, 6.02 1H d, J=2.4 Hz, 5.98 1H d, J=2.4, 5.61 1H s, 4.37 1H, m, 3.03 1H dd, J=4.8, 16.8 Hz, 2.87 d, J=16.8 Hz; $^{13}$C NMR (CD$_3$OD, 150 MHz): $\delta_C$ 186.5, 170.1, 167.1, 158.0, 156.9, 155.1, 151.7, 148.9, 146.2, 139.8, 132.8, 131.6, 126.8, 122.6, 122.5, 120.8, 116.3, 110.0, 99.3, 96.9, 96.0, 75.7, 68.6, 27.2 ppm.

13. EGCCa

EGC (1 g) and catechol (1.5 g) were dissolved in a mixture of acetone-pH 5.0 phosphate citrate buffer (1:10, v/v, 50 mL), which contained 2 mg horseradish peroxidase. While being stirred, 2.0 ml of 3.13% $H_2O_2$ was added four times during 45 minutes. The reaction mixture was extracted by ethyl acetate (50 mL×3). After concentration, the residue was subjected to Sephadex LH 20 column eluted with acetone-water solvent system (45%). 226 mg EGCCa was obtained.

$^1$H NMR (C$_5$D$_5$N, 600 MHz): $\delta_H$ 8.15 1H s, 7.99 1H s, 7.66 1H d, J=8.4 Hz, 7.41 1H d, J=8.4 Hz, 6.75 1H brs, 6.74 1H brs, 5.23 1H s, 4.76 1H, s, 3.67 d, J=16.2 Hz, 3.44 dd, J=3.6, 16.2 Hz; $^{13}$C NMR (C$_5$D$_5$N, 150 MHz): $\delta_C$ 184.9, 158.8, 157.2, 151.8, 151.4, 147.8, 134.6, 134.5, 132.0, 126.4, 123.3, 121.2, 119.9, 119.8, 9 9.9, 97.1, 96.0, 81.8, 66.6, 30.3 ppm.

14. EGCGCa

EGCG (1 g) and catechol (1.5 g) were dissolved in a mixture of acetone-pH 5.0 phosphate citrate buffer (1:10, v/v, 50 mL), which contained 2 mg horseradish peroxidase. While being stirred, 2.0 mL of 3.13% $H_2O_2$ was added four times during 45 minutes. The reaction mixture was extracted by ethyl acetate (50 ml×3). After concentration, the residue was subjected to Sephadex LH 20 column eluted with acetone-water solvent system (45%). 230 mg EGCGCa (Epigallocatechinocatechol gallate) was obtained.

$^1$H NMR (C$_5$D$_5$N, 600 MHz): $\delta_H$ 8.01 1H s, 7.97 1H s, 7.54 1H d, J=8.4 Hz, 7.29 1H d, J=8.4 Hz, 6.74 1H d, J=2.4 Hz, 6.70 1H d, J=2.4, 6.18 1H s, 5.38 1H, s, 3.71 d, J=17.4 Hz, 3.51 dd, J=3.0, 17.4 Hz; $^{13}$C NMR (C$_5$D$_5$N, 150 MHz): $\delta_C$ 185.0, 166.8, 159.0, 158.8, 156.9, 155.4, 151.9, 148.1, 147.7, 141.4, 134.5, 133.0, 131.6, 126.4, 123.2, 121.2, 120.8, 118.8, 110.4, 98.9, 97.5, 96.0, 80.1, 69.1, 27.5 ppm.

15. GACa

Gallic acid (2 g) and catechol (2 g) were dissolved in a mixture of acetone-pH 5.0 phosphate citrate buffer (1:10, v/v, 50 mL), which contained 4 mg horseradish peroxidase. While being stirred, 2.0 ml of 3.13% $H_2O_2$ was added four times during 45 minutes. The reaction mixture was extracted by ethyl acetate (50 mL×3). After concentration, the residue was subjected to Sephadex LH 20 column eluted with acetone-water solvent system (45%). 400 mg GACa was obtained.

$^1$H NMR (C$_5$D$_5$N, 600 MHz): $\delta_H$ 8.08 1H brs, 7.68 1H dd, J=1.2, 8.4 Hz, 7.56 1H d, J=8.4 Hz, 7.19 1H s; $^{13}$C NMR (C$_5$D$_5$N, 150 MHz): $\delta_C$ 186.0, 169.6, 154.8, 152.6, 150.5, 140.0, 130.2, 128.8, 125.6, 123.0, 121.6, 117.9 ppm.

16. Purpurogallin

Pyrogallol (1 g) and catechol (1.5 g) were dissolved in a mixture of acetone-pH 5.0 phosphate citrate buffer (1:10, v/v, 50 mL), which contained 2 mg horseradish peroxidase. While being stirred, 2.0 mL of 3.13% $H_2O_2$ was added four times during 45 minutes. The reaction mixture was extracted by ethyl acetate (50 mL×3). After concentration, the residue was subjected to Sephadex LH 20 column eluted with acetone-water solvent system (45%). 300 mg Purpurogallin was obtained.

$^1$H NMR (C$_5$D$_5$N, 600 MHz): $\delta_H$ 7.35 1H d, J=11.4 Hz, 7.29 1H s, 7.24 1H d, J=9.6 Hz, 6.66 1H dd, J=9.6, 11.4 Hz; $^{13}$C NMR (C$_5$D$_5$N, 150 MHz): $\delta_C$ 183.4, 156.3, 154.0, 153.3, 137.1, 135.1, 134.4, 123.8, 116.8, 116.2, 112.0 ppm.

17. Purpurogallin Carboxylic Acid $^1$H NMR (CD$_3$OD, 600 MHz): $\delta_H$ 8.17 1H s, 7.66 1H s, 6.94 1H s; $^{13}$C NMR (CD$_3$OD, 150 MHz): $\delta_C$ 184.0, 170.0, 156.6, 154.4, 153.2, 152.2, 137.8, 134.2, 125.9, 123.0, 116.3, 114.5 ppm.

Of the seventeen compounds synthesized above, Neotheaflavate B (compound 9) and EGCGCa (compound 14) are novel compounds not known in the art. The rest of the compounds are known in the art, i.e., compounds 1–8, 10–12 have been identified from black tea, compounds 13, 15–17 have been reported through chemical oxidation method, but the prior art known compounds were synthesized by methods other than the peroxidase catalyzed oxidative reactions.

Thus, seventeen different benzotropolone containing compounds were synthesized by Peroxidase/H$_2$O$_2$ system.

B. Synthesis of Benzotropolone Containing Compounds Catalyzed by Polyphenol Oxidase (PPO)

Crude polyphenol oxidase (PPO)was isolated from banana fruits purchased from a local market. Briefly, a fresh banana (400 g) was homogenized with 800 mL of cold 100 mM phosphate buffer (pH 7.0, 4° C.). The homogeneous solution was centrifuged at 4° C. for 20 min (10,000 g). The clear supernatant was carefully collected into the flask which is placed in the ice bath. Then, the same volume of cold acetone, which is kept in the freezer for overnight, was slowly added into the collected solution with stirring. The resulting protein precipitates were collected by centrifugation at 4° C. (10,000 g, 20 min). After centrifugation, supernatant was discarded, and the resulting pellet was carefully washed with the 0.1 M phosphate buffer (pH 7.0) for three times. Then, the pellets were dissolved with the same buffer and freeze-dried.

Enzyme activity was measured by colorimetric method. The enzyme reaction solution consisted of 2 mL of 0.1 M catechol solution and 1 mL of phosphate buffer (50 mM, pH 7.0) and 20 μL of the enzyme solution. The enzyme activity was measured at 420 nm for 5 min (25° C.) with increasing the absorbance. The PPO activity was defined as the amount of enzyme of increasing the absorbance of 0.001 per minute.

With the PPO catalyzed oxidative reaction, 9 compounds were synthesized as described in the paragraphs below. The compound numbers referred to in this section correspond to the compound numbers under part III, A above under the examples section.

1. Enzymatic Oxidation and Isolation of Theaflavins

EC (1 g, 3.5 mmol) and EGC (1 g, 3.3 mmol) were dissolved into the 200 mL of phosphate-citrate buffer (50 mM, pH 5.0) along with 2 g of crude PPO enzyme. The enzymatic oxidation was carried out at room temperature for 6 hour with stirring. The reaction solution was then subjected to fractionation with the same volume of ethyl acetate with three times. Then, the organic layer was concentrated under reduced pressure. The resulting residues were subjected to Sephadex LH-20 column chromatography eluting with gradient of ethanol to 20% of acetone in ethanol. Among the collected 14 fractions (each c.a. 90 mL), 8~10 fractions were combined, and concentrated under reduced pressure. The resulting residue was subjected to further purification on a RP-18 silica gel column eluting with gradient of 40%~50% of aqueous methanol. During elution, 38 fractions (each c.a. 13 mL) were received. Among them, 10~17 fractions were combined, and concentrated under reduced pressure, and were subjected to freeze-drying. It yielded deep-reddish color of compound 1 (280 mg). Along with the same enzyme reaction and isolation procedure, compound 2 was obtained from EC and EGCG reaction. The enzymatic oxidation of EGC and ECG, ECG and EGCG reaction yielded compound 3 and compound 4, respectively.

2. Enzymatic Reaction of Tea Catechins (EC and ECG) and Gallic Acid

EC (1.160 g, 4.0 mmole) and gallic acid (0.520 g, 4.0 mmole) were dissolved in the 100 mL of phosphate-citrate buffer (50 mM, pH 5.0), and 1.2 g of crude PPO enzyme was added into the reaction solution with stirring. The enzymatic oxidation was carried out at room temperature for 3.5 hour. After the reaction, the solution extracted with the same volume of ethyl acetate with three times. Then, the ethyl acetate extracts was concentrated in vacuo. The resulting residues were then subjected to Sephadex LH-20, eluting with gradient of ethanol to 20% of acetone in ethanol. Among the collected 168 (each c.a. 15 mL) fractions, 47~52 fractions were combined, and it was concentrated under reduced pressure. The resulting residue was applied on a RP-18 silica gel column eluting with gradient of 20%~50% of aqueous methanol, and it was afforded compound 5. Then, 72~85 fractions, isolated from Sephadex LH-20, were combined, and it was subjected to RP-18 column chromatography eluting with gradient of 10%~50% of aqueous methanol, and compound 6 was isolated.

ECG (0.66 g) and gallic acid (0.26 g) were dissolved in the 50 mL of phosphate-citrate buffer (50 mM, pH 5.0), and 1.2 g of crude PPO enzyme was dissolved in the reaction solution. The enzymatic oxidation was performed at room temperature for 5 hour. The reaction solution was then extracted with ethyl acetate with three times. Then, the organic layer was concentrated under reduced pressure. The resulting residues were subjected to Sephadex LH-20 column chromatography eluting with gradient of ethanol to 20% of acetone in ethanol. Among the collected 128 fractions (each c.a. 15 mL), 18~20 fractions were combined, and concentrated under reduced pressure. The resulting residue was subjected for further purification on a RP-18 silica gel column eluting with gradient of 20%~50% of aqueous methanol, and afforded compound 7. The 37~48 fractions were combined and subjected to RP-18 column chromatography for further purification eluting with gradient of 10%~30% of aqueous methanol, and afforded compound 8. The 90~108 fractions were combined and subjected to RP-18 column chromatography eluting with gradient of 40%~50% of aqueous methanol, and it was then afforded compound 9.

IV. Oxygen-Radical Absorbance Capacity (ORAC) Assay

Oxygen radical absorbance capacity (ORAC) assay was performed to examine antioxidant activity of individual theaflavins and epitheaflavic acids. All reagents were prepared in 75 mM phosphate buffer (pH 5.5). Reaction mixture consists of 3 mL of Fluorescein solution (8.16×10$^{-5}$ mM), 500 μL AAPH (153 mM), and 500 μL of sample solution or blank. Once AAPH was added, fluorescence was measured every 1 min using Hitachi Model F-3010 fluorescence spectrophotometer with emission and excitation wavelength of 515 and 493 nm, respectively. The ORAC value was calculated based on the area under the fluorescence decay curve of fluorescein in the presence of the test compound comparing to the area generated by standard Trolox and blank. The net area under the curve and ORAC values were calculated by the formula presented by Cao et al (Cao et al. 1993).

The relative ORAC value (Trolox equivalents) was calculated with following equation.

Relative $ORAC$ value = $[(AUC_{sample} - AUC_{blank})/(AUC_{Trolox} - AUC_{blank})] \times$ (molarity of Trolox/molarity of sample)

The area under curve (AUC) was calculated according to following equation.

$AUC = 1 + f_1/f_0 + f_2/f_0 + f_3/f_0 + f_4/f_0 \ldots + f_{119}/f_0 + f_{120}/f_0$ $f_0$ is the initial fluorescence reading at 0 min, $f_i$ is the fluorescence reading at time i.

Quenching curves representing the peroxyl radical absorbing activity of Trolox in various concentration (0~4 μM) was used as a standard (data not shown). The net area of quenching curve increased proportionally to an increment of the Trolox concentration. Quenching curves of theaflavins and EGCG were examined (data not shown). At the same concentration (0.5 μM) tested, the ORAC values (Table 1) revealed that theaflavins had higher antioxidant activity than EGCG. Quenching curves of epitheaflavic acids and EGCG were also examined. (data not shown). The ORAC value (Table 2) of epitheaflavic acids revealed that these compounds had slightly higher antioxidant activity than those of EGCG.

TABLE 1

Relative ORAC values of theaflavins, epitheaflavic acids and EGCG

| Compounds | Relative ORAC value |
|---|---|
| Theaflavin | 11.60 ± 0.30 |
| Theaflavin-3-gallate | 13.17 ± 0.18 |
| Theaflavin-3'-gallate | 12.40 ± 0.58 |
| Theaflavin-3,3'-gallate | 13.54 ± 0.69 |
| Epitheaflavic acid[a] | 9.74 ± 0.38 |
| Purprogallin[a] | 6.01 ± 0.42 |
| EGCG | 7.69 ± 0.35 |

Data are expressed as the mean ± SD,
n = 4,
[a]n = 3

V. Anti-Inflammatory Activity of Benzotropolone Containing Compounds

The TPA (12-O-tetradecanoylphorbol-13-acetate)-induced ear edema assay was carried out to examine anti-inflammatory activity of benzotropolone-containing compounds in skin inflammation model. The female CD-I mice (24-25 days old) were topically treated with 20 μl of acetone and benzotropolone-containing compounds in 20 μl of acetone at 20 minutes before topical application of 20 μl of acetone or TPA (1 nmol) in 20 μl of acetone. Then, five hours later, all mice were sacrificed by cervical dislocation. The ear punches (6 mm in diameter) were taken and weighed.

The results are shown in Table 2 below. The various benzotropolone containing compounds showed strong inhibitory effect.

TABLE 2

Inhibitory Effect of Theaflavin Type Compounds on TPA-induced Edema of Mouse Ear

| Treatment | Average weight of ear punches (mg) (Mean ± SE) | Percent inhibition % |
|---|---|---|
| Acetone + Acetone | 7.44 ± 0.08* | — |
| Acetone + TPA (1 nmol) | 11.7 ± 1.38 | — |
| Theaflavin (0.5 μmol) + TPA (1 nmol) | 7.90 ± 0.42* | 89.2 |
| Theaflavin 3-gallate (0.5 μmol) + TPA (1 nmol) | 7.86 ± 0.24* | 91.5 |
| Theaflavin 3'-gallate (0.5 μmol) + TPA (1 nmol) | 7.44 ± 0.18* | 100.0 |
| Theaflavin 3,3'-gallate (0.5 μmol) + TPA (1 nmol) | 7.03 ± 0.18* | 100.0 |
| EGCG (0.5 μmol) + TPA (1 nmol) | 8.79 ± 0.54* | 68.3 |
| Acetone + Acetone | 7.44 ± 0.07* | — |
| Acetone + TPA (1 nmol) | 15.91 ± 0.51 | — |
| Theaflavate B (0.5 μmol) + TPA (1 nmol) | 8.35 ± 0.32* | 89.2 |
| Theaflavate A (0.5 μmol) + TPA (1 nmol) | 8.52 ± 0.26* | 87.2 |
| Neotheaflavate A (0.5 μmol) + TPA (1 nmol) | 8.65 ± 0.64 | 85.7 |
| Neotheaflavin (0.5 μmol) + TPA (1 nmol) | 10.58 ± 0.73 | 62.9 |
| Neotheaflavin 3-gallate (0.5 μmol) + TPA (1 nmol) | 8.42 ± 0.42* | 88.4 |
| Theaflavic acid (0.5 μmol) + TPA (1 nmol) | 9.28 ± 0.37* | 78.3 |
| Acetone + Acetone | 7.17 ± 0.18* | — |
| Acetone + TPA (1 nmol) | 15.85 ± 0.86 | — |
| Theaflavic acid (0.5 μmol) + TPA (1 nmol) | 8.95 ± 0.43* | 79.5 |
| Epitheaflavic acid (0.5 μmol) + TPA (1 nmol) | 9.39 ± 0.43* | 74.4 |
| GACa (0.5 μmol) + TPA (1 nmol) | 8.61 ± 0.54* | 83.3 |
| EGCCa (0.5 μmol) + TPA (1 mnol) | 7.86 ± 0.18* | 92.1 |
| EGCGCa (0.5 μmol) + TPA (1 nmol) | 7.49 ± 0.12* | 96.3 |
| Theaflavin (0.5 μmol) + TPA (1 nmol) | 8.23 ± 0.40* | 87.8 |

These results are unexpected given the recent report by Liang et al., 2002, Nutrition and Cancer 42(2); 217–223. Liang compared the anti-inflammatory activity of three major theaflavins in black tea. Three compounds they studies were TF-1 (i.e., theaflavin, compound 1 in the example above), TF-2 (i.e., a mixture of Theaflavin 3-gallate and Theaflavin 3'-gallate, mixture of compounds 2 and 3 in the example above) and TF-3 (i.e., Theaflavin 3,3'-digallate, compound 4 in the example above). The anti-inflammatory test method used in Liang was the same as we used in the present invention. From the results of Liang et al. study shown in Table 1, it is clear that the anti-inflammatory activity of TF-3 should be stronger than TF-2, and TF-2 should be stronger than TF- 1.

All publications, patents and patent applications mentioned in this specification are indicative of the level of those skilled in the art to which this invention pertains. The contents of all the publications, patents and patent applications are incorporated herein by reference to the same extent as if each individual publication, patent or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. Neotheaflavate B or a salt or an ester thereof.

2. EGCGCa (Epigallocatechinocatechol gallate) or a salt or an ester thereof.

3. A composition comprising the neotheaflavate B or a salt or an ester thereof of claim 1.

4. A composition comprising the EGCGCa or a salt or an ester thereof of claim 2.

5. The composition of claim 4, further comprising a pharmaceutically acceptable carrier or diluent, wherein said composition is effective as an anti-inflammatory agent or antioxidant.

6. The composition of claim 4, wherein the composition is a nutraceutical and is effective as an anti-inflammatory agent or antioxidant.

7. The composition of claim 3, wherein the composition is a nutraceutical and is effective as an anti-inflammatory agent or antioxidant.

8. The composition of claim 3, further comprising a pharmaceutically acceptable carrier or diluent, wherein said composition is effective as an anti-inflammatory agent or antioxidant.

9. A method for treating an inflammatory condition comprising administering to a subject in need thereof a composition comprising an amount of (i) neotheaflavate B, a salt or an ester thereof; or (ii) EGCGCa (epigallocatechinocatechol gallate), a salt or an ester thereof, wherein said amount is effective to treat the inflammatory condition.

10. The method according to claim 9 wherein said amount is at a dosage of between about 0.5 and about 1000 mg per kilogram body weight per day.

11. The method according to claim 9 wherein said amount is at a dosage of between about 1 and about 500 mg per kilogram body weight per day.

12. The method according to claim 9 wherein said composition is administered topically.

13. The method according to claim 9 wherein said composition is administered orally.

14. The method according to claim 9 wherein said composition is administered parenterally.

15. A method of treating or reducing the progression of an inflammatory condition comprising administering to a subject in need thereof a composition comprising an effective amount of (i) neotheaflavate B, a salt or an ester thereof; or (ii) EGCGCa (epigallocatechinocatechol gallate), a salt or an ester thereof, and a carrier selected from the group consisting of a pharmaceutically acceptable carrier, veterinary acceptable carrier, dietary supplement carrier and food.

16. The method of claim 15, wherein the carrier is a pharmaceutically acceptable carrier.

17. The method of claim 15, wherein the subject is a human.

18. The method of claim 15, wherein the carrier is a food.

19. The method of claim 15, in which the composition is a dietary supplement.

20. A method for neutralizing free radicals in a patient comprising: administering to the patient in need of such treatment a composition comprising an effective amount of (i) neotheaflavate B, a salt or an ester thereof; or (ii) EGCGCa (epigallocatechinocatechol gallate), a salt or an ester thereof.

21. The method of claim 20, wherein the neotheaflavate B or EGCGCa (epigallocatechiflocatechol gallate), a salt or an ester thereof is present at a concentration of at least about 0.5%.

22. The method of claim 20, wherein the composition comprises neotheaflavate B, a salt or an ester thereof.

23. The method of claim 20, wherein the composition comprises EGCGCa (epigallocatechinocatechol gallate), a salt or an ester thereof.

24. The method of claim 20, wherein the composition comprises a carrier selected from the group consisting of a pharmaceutically acceptable carrier, veterinary acceptable carrier, dietary supplement carrier and food.

25. The neotheaflavate B, a salt or an ester thereof of claim 1, which is purified.

26. The EGCGCa (Epigallocatechinocatechol gallate), a salt or an ester thereof of claim 2, which is purified.

* * * * *